United States Patent
Hegedusch

Patent Number: 5,121,755
Date of Patent: Jun. 16, 1992

[54] REINFORCED TETHERED CONDOM CONSTRUCTION

[76] Inventor: Joseph Hegedusch, Rte. 1, Box 318, Luray, Va. 22835

[21] Appl. No.: 773,812

[22] Filed: Oct. 9, 1991

[51] Int. Cl.⁵ .......................... A61F 6/04; A61F 5/00
[52] U.S. Cl. .................................. 128/844; 128/918
[58] Field of Search ............... 128/842, 844, 79, 918; 604/330, 347-353

[56] References Cited

U.S. PATENT DOCUMENTS

| | | | |
|---|---|---|---|
| 2,610,630 | 9/1952 | Crew | 604/347 |
| 3,018,484 | 1/1962 | Koehn | 128/844 |
| 3,759,254 | 9/1973 | Clark | 128/79 |
| 3,893,455 | 7/1975 | McNally | 128/79 |
| 4,354,494 | 10/1982 | Hogin | 128/844 |
| 4,429,689 | 2/1984 | Yanong | 128/79 |
| 4,731,064 | 3/1988 | Heyden | 604/352 |
| 4,881,553 | 11/1989 | Grossman | 128/844 |
| 4,895,140 | 1/1990 | Bellak | 128/79 |
| 4,906,242 | 3/1990 | Thomas | 128/844 |
| 4,966,594 | 10/1990 | Thomas | 604/349 |
| 4,971,071 | 11/1990 | Johnson | 128/844 |

FOREIGN PATENT DOCUMENTS 0267218 11/1913 Fed. Rep. of Germany ...... 604/349

*Primary Examiner*—Robert A. Hafer
*Assistant Examiner*—Michael Brown
*Attorney, Agent, or Firm*—Henderson & Sturm

[57] ABSTRACT

A reinforced tethered condom construction (10) for male genitalia (100); wherein, the condom construction (10) comprises a conventional condom sheath (20) which is provided with a pair of elongated tether elements (30) secured on the inside (21) of the condom sheath (20) to provide lateral reinforcement along a substantial portion of the condom sheath (20); and, wherein the free ends of the tether elements (30) are dimensioned to both encircle and be secured to the users genitalia.

7 Claims, 1 Drawing Sheet

REINFORCED TETHERED CONDOM CONSTRUCTION

BACKGROUND ART

As can be seen by reference to the following U.S. Pat. Nos. 3,759,254; 4,354,494; 4,881,553; and 4,906,242; the prior art is replete with myriad and diverse condom constructions that are equipped either with tethering means or with reinforcing means.

While all of the aforementioned prior art constructions are more than adequate for the basic purpose and function for which they have been specifically designed, these patented constructions are uniformly deficient with regard to the facts that to date no one has produced a condom construction that employs both tethering and reinforcing means in a single condom construction, nor do the condom manufacturers take into account the problems that are encountered by males who are at a minimum to be politely described as generously endowed.

As a consequence of the foregoing situation, there has existed a longstanding need not only among the small segment of males who are blessed by nature as it were, but also to the male population in general for a new type of condom construction that employs both reinforcement to the walls of the condom but also a means of securely fastening the condom to their genitals; and, the provision of such a construction is a stated objective of the present invention.

DISCLOSURE OF THE INVENTION

Briefly stated, the condom construction that forms the basis of the present invention comprise a conventional condom sheath which is reinforced by the presence of two elongated tether elements which are disposed in a laterally opposed orientation on the interior of the condom sheath and which extend a selected distance beyond the end of the sheath.

In addition, the tether elements also extend a minimum distance within the sheath interior to provide lateral support along a substantial portion of the total length of the sheath.

As will be explained in greater detail further on in the specification, the positioning of the tether elements on the interior of the sheath is specifically designed not only to provide the reinforcement support where it is needed the most, since most incidences of sheath rupturing occur along the intermediate portion of the sheath; but also to minimize any frictional irritation to the males partner attributable to the presence of the tether elements, since the tether elements remain stationary relative to the person wearing the sheath.

In addition the minimum length that is chosen to extend beyond the open end of the sheath was selected so as to insure that the tether elements would have an adequate length to encircle and be secured around even very large male genitalia.

BRIEF DESCRIPTION OF THE DRAWINGS

These and other attributes of the invention will become more clear upon a through study of the following description of the best mode for carrying out the invention, particularly when reviewed in conjunction with the drawings, wherein.

BEST MODE FOR CARRYING OUT THE INVENTION

Figure 1:
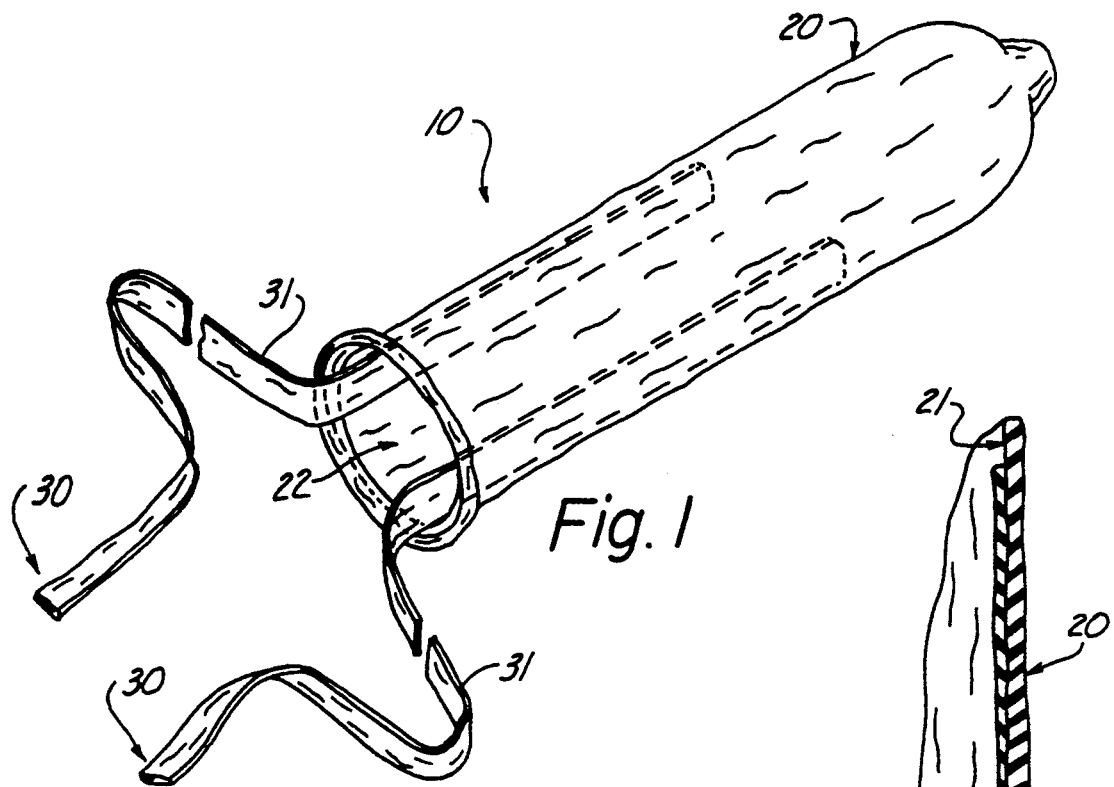
FIG. 1 is a perspective view of the reinforced tethered condom construction that forms the basis of the present invention deployed on male genitalia; and, FIG. 2 is an isolated top plan view of the condom construction.

As can be seen by reference to the drawings, and in particular to FIG. 1, the reinforced tethered condom construction that forms the basis of the present invention is designated generally by the reference numeral (10).

Figure 2:
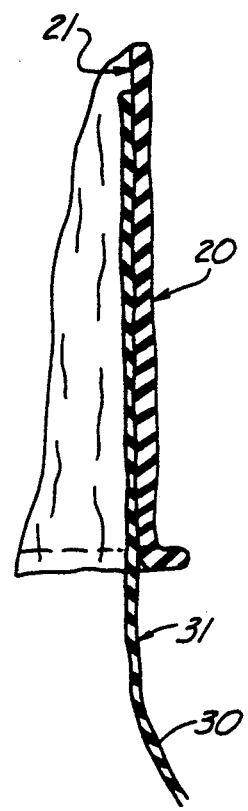

As shown in FIGS. 1 and 2 the condom construction (10) comprises a conventional condom sheath (20) whose overall performance and function in its intended manner is dramatically enhanced by the presence of a pair of tether elements (30) which are operatively connected to the condom sheath (20) to proved both reinforcement for the sheath per se; as well as a means of securely fastening the sheath to the male genitalia (100) to prevent the sheath from coming off during intercourse.

Figure 3:
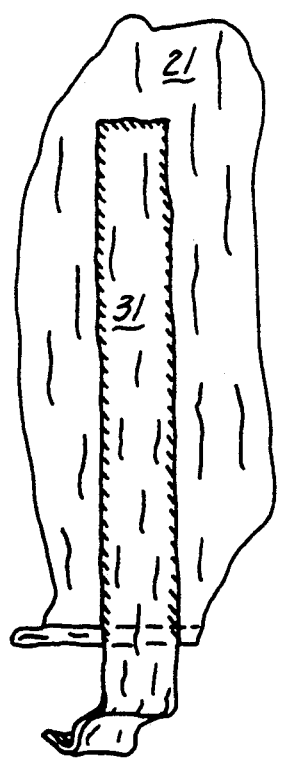
FIG. 3 is an isolated detail view of the reinforcement.

As can best be seen by reference to FIG. 2 and FIG. 3, the tether elements (30) comprise elongated lengths of generally thin flat ribbon-like material (31) which are operatively secured in an opposed orientation on the interior walls (21) of the condom sheath (20) via suitable securing means, such as non-toxic adhesives or the like.

In addition in the preferred embodiment of the invention, the ribbon-like material (31) the preferred width and thickness of the ribbon-like material (31) are 5 mm and 1 mm respectively to minimize the frictional profile of the thickness of the tether elements (30); as well as, still provide a sufficient width that will allow the user to grasp, manipulate, and tie the tether elements (30) around their genitalia.

Still referring to FIG. 2, it can be appreciated that the preferred embodiment of this invention requires that the secured portion of the tether elements extend into the interior (21) of the condom sheath (20) a minimum of ¾ of the length of the condom sheath (20) so as to provide lateral reinforcement along at least a substantial portion of the condom sheath (20).

In addition, as was mentioned previously since this particular condom construction (10) was specifically designed to combat the problems encountered by generously endowed males, the minimum length that the tether elements (30) will extend beyond the open end (22) of the condom sheaths (20) will be 12 inches.

Figure 4:
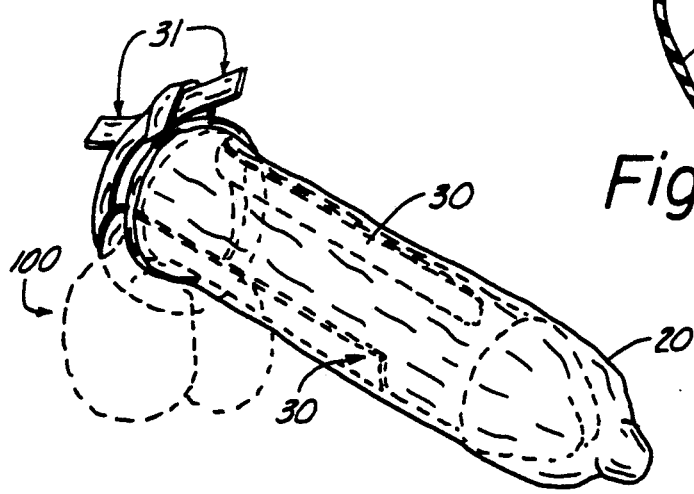
FIG. 4 shows the construction in its operative mode of depolyment.

The reason for this minimum length is depicted in FIG. 4, wherein, the free ends of the tether elements (30) are intended to criss-cross behind the users testicles and be wrapped around the users penis and testicles at least one complete revolution before being tied together on top of the users penis.

Having thereby described the subject matter of the present invention, it should be apparent that many substitutions. modifications and variations of the invention are possible in light of the above teachings. It is therefore to be understood that the invention as taught and described herein is only to be limited to the extent of the breadth and scope of the appended claims.

I claim:

1. A reinforced tethered condom construction designed particularly for males equipped with large genitalia: wherein the condom construction consists of:
   a conventional condom sheath; and,
   a pair of elongated generally thin, flat tether elements, each having one end secured to the interior of the condom sheath in an opposed fashion; wherein, the securement further occurs along a main portion of the length of the condom sheath to provide lateral and longitudinal reinforcement thereto; and, further having a free end which extends a predetermined minimum distance beyond the open end of the condom sheath, so that the free ends of the tether elements can encircle and be secured to the male genitalia.

2. The condom construction as in claim 1; wherein the said predetermined minimum distance from the open end of the condom sheath is approximately twice the length of the condom sheath.

3. The condom construction as in claim 2; wherein, the said substantial portion of the condom sheath comprises at least three-fourths of the length of the condom sheath.

4. The condom construction as in claim 1; wherein, the said predetermined minimum distance from the open end of the sheath is a minimum distance of twelve inches.

5. The condom construction as in claim 1; wherein, the tether elements each comprise elongated, thin, flat, lengths of ribbon-like material.

6. The condom construction as in claim 5; wherein, the minimum thickness of the ribbon-like material is approximately 1 mm.

7. The condom construction as in claim 6; wherein, the minimum width of the ribbon-like material is approximately 5 mm.

* * * * *